(12) United States Patent
Mezzoli

(10) Patent No.: US 6,701,916 B2
(45) Date of Patent: Mar. 9, 2004

(54) DISTRIBUTION VALVE FOR NASAL SPRAY

(76) Inventor: Giorgio Mezzoli, via Ricci Curbastro, 56/I, 48022 Lugo (IT)

( * ) Notice: Subject to any disclaimer, the term of this patent is extended or adjusted under 35 U.S.C. 154(b) by 0 days.

(21) Appl. No.: 10/312,480

(22) PCT Filed: Jun. 26, 2001

(86) PCT No.: PCT/EP01/07285

§ 371 (c)(1),
(2), (4) Date: Dec. 23, 2002

(87) PCT Pub. No.: WO02/00282

PCT Pub. Date: Jan. 3, 2002

(65) Prior Publication Data

US 2003/0101992 A1 Jun. 5, 2003

(30) Foreign Application Priority Data

Jun. 26, 2000 (IT) ...................... MI2000A1433

(51) Int. Cl.[7] .............................................. A61M 11/00
(52) U.S. Cl. ............................ 128/200.22; 128/200.14; 128/203.28
(58) Field of Search ....................... 128/200.14, 200.22, 128/200.23, 203.28

(56) References Cited

U.S. PATENT DOCUMENTS

| 4,513,891 | A |   | 4/1985  | Hain et al.      |            |
|-----------|---|---|---------|------------------|------------|
| 4,944,429 | A |   | 7/1990  | Bishop et al.    |            |
| 5,031,800 | A | * | 7/1991  | Brunet           | 222/153.06 |
| 5,505,193 | A | * | 4/1996  | Ballini et al.   | 128/200.15 |
| 5,829,434 | A | * | 11/1998 | Ambrosio et al.  | 128/203.15 |
| 6,065,474 | A | * | 5/2000  | Coe              | 128/205.23 |
| 6,418,924 | B1| * | 7/2002  | Poley et al.     | 128/200.14 |

FOREIGN PATENT DOCUMENTS

| DE |     2123252 | 1/1973  |
|----|-------------|---------|
| FR |   1.211.726 | 3/1960  |
| WO | WO 99/49984 | 10/1999 |

* cited by examiner

*Primary Examiner*—Weilun Lo
*Assistant Examiner*—Michael Mendoza
(74) *Attorney, Agent, or Firm*—Abelman, Frayne & Schwab

(57) ABSTRACT

A distribution valve for nasal spray allowing to distribute a drug inside the nasal cavities in a uniform and repeatable way is described. The distribution valve has a section of elliptical or oval shape, corresponding to the shape of the nostril and it has a distribution nozzle having elliptical or oval shape (or slot shape) in order to obtain a more uniform distribution of the medicament on the inner mucosa of the nasal cavity.

6 Claims, 5 Drawing Sheets

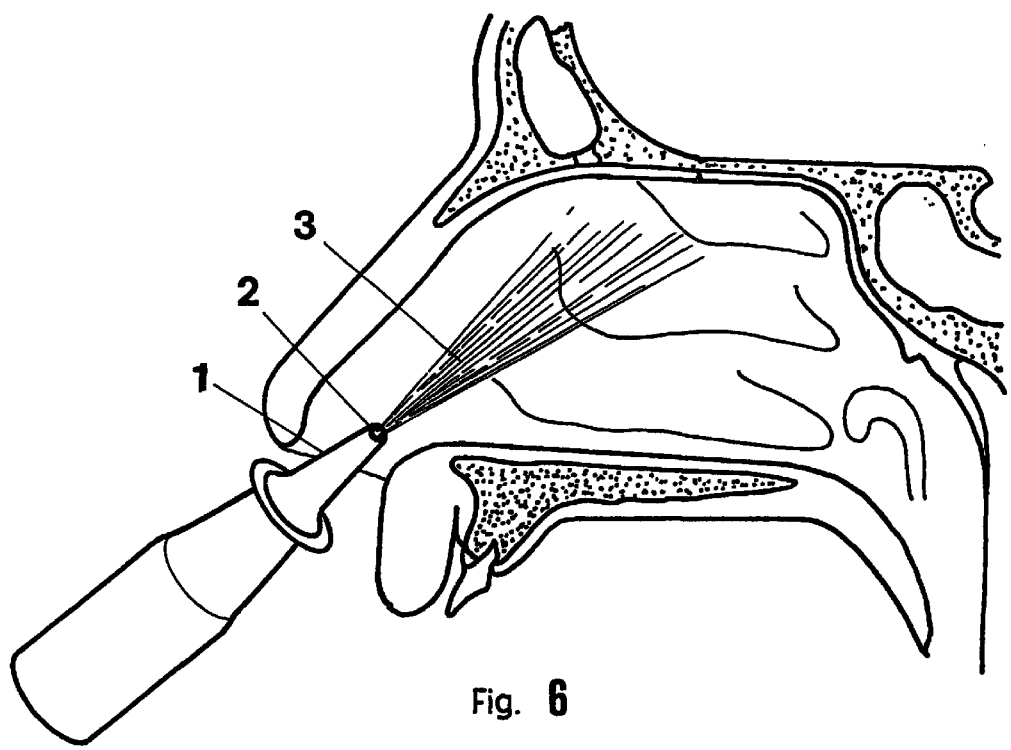
Fig. 6
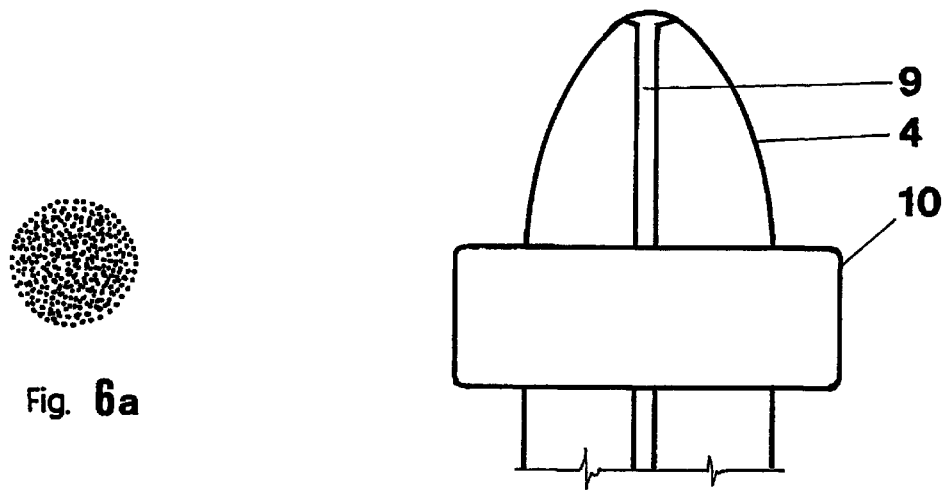
Fig. 6a
Fig. 7a
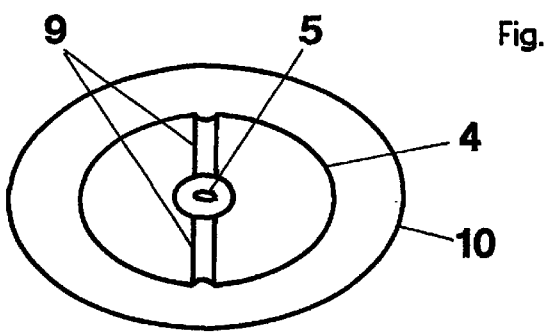
Fig. 7b

DISTRIBUTION VALVE FOR NASAL SPRAY

This application is filed pursuant to 35 U.S.C. §371 as a United States National Phase Application of Ser. No. PCT/EP01/07258 filed Jun. 26, 2001, which claims priority from MI2000A001433 filed Jun. 26, 2000 in Italy.

FIELD OF THE INVENTION

The invention consists in a distribution valve for nasal spray having a section of elliptical or oval shape and showing a distribution nozzle having elliptical or oval shape or slot shape.

PRIOR ART

Applying inside the nasal cavities drugs in "spray" form either for preventive purpose (for example, in order to prevent and/or mitigate allergic syndromes and/or their manifestations) or for curative purpose, for example to treat diseases of the nasal cavities (rhinitises, sinusitises, and so on) and/or to make the patient take by the nasal mucosas drugs assigned to carry out their action in other body regions is a well known and widely consolidated practice.

The drugs normally taken in "nasal spray" form and the pursued (or which may be pursued) aims by the intake of such drugs will not be further discussed here because known by themselves and however extraneous to the present invention; such drugs, normally contained in an aerosol bomb or other airtight container, are vehiculated by a fluid (gas, air, and so on) and they are applied to the nasal mucosa by a distribution valve fixed to the drug container.

In the present description, with "distribution valve" we mean globally the means, carried by the container, enabling to apply "in loco" the drug and the means (not further described because known by themselves) allowing to control and to dose the delivery of the drug.

In the distribution valves of known kind the means to apply "in loco" the drug normally include a cylindrical or truncated conical body, to be inserted into a nostril, at the end of which there is a round, very small sized, distribution nozzle normally located at the longitudinal symmetry axis of the above mentioned body: the drug is expelled under pressure (in a known by itself manner) through the distribution nozzle and the jet coming out from the distribution nozzle is directed varying the inclination angle of the longitudinal symmetry axis of the cylindrical or truncated conical body inside the nasal cavity.

Numerous studies and experimental checks showed that a drug is more effective if it is distributed into the nasal cavity in an extended, uniform and repeatable way, that is uniformly distributed on a wide zone of the nasal mucosa that is, however possible, the same on each application.

The distribution valves of known kind turned out not to be particularly suitable to satisfy such need, because:

the substantially axial direction of the jet having conical shape coming out from the distribution nozzle allows to spray a limited portion of the nasal mucosa, as shown in FIG. 6; in order to spray the whole nasal mucosa one has to spray the drug two or three times, varying the inclination angle of the longitudinal symmetry axis of the cylindrical or truncated conical body within the nasal cavity;

the substantially cylindrical or truncated conical shape of the body carrying the distribution nozzle fits poorly the substantially elliptical or oval section of a nostril (into which it may be inserted from time to time with different angle) and it does not allow therefore to direct, on each application, the jet supplied by the nozzle to the same portion of the nasal mucosa; moreover the need to obtain a uniform distribution of the drug on the whole mucosa of the nasal cavity varying the inclination angle of the longitudinal symmetry axis of the above mentioned body inside the nasal cavity involves (or may involve) the risk to damage the mucosa of the nasal septum or the nasal turbinates one, causing bleedings and/or other injuries.

The distribution valve for nasal spray object of the present invention allows to obtain a wider, more uniform and more repeatable, distribution of the medicament inside the nasal cavities proving to be free from the above mentioned drawbacks presented by the distribution valves of known kind.

SUMMARY OF THE INVENTION

The object of the present invention is a distribution valve for nasal spray including a body, to be inserted into a nostril, having a section of elliptical or oval shape (preferably having size equivalent to the nostril one); at the end of the above mentioned body of elliptical or oval section there is a distribution nozzle having elongated (elliptical or oval or slot shaped) form.

By elliptical or oval section we mean a section having a major symmetry axis and a minor symmetry axis, wherein the major axis has a length different from the minor axis one.

BRIEF DESCRIPTION OF THE FIGURES

The invention will be better described referring to embodiment examples not having limitative character illustrated in the appended Figures, wherein:

FIG. 6 schematically shows an anatomical section showing the jet coming out from a distribution nozzle of known kind and its propagation inside the nasal cavity;

FIG. 7 shows a side (FIG. 7a) view and a top (FIG. 7b) view of a distribution valve realized according to the invention, differing from the FIG. 2 one in that its top end is rounded;

DETAILED DESCRIPTION OF THE INVENTION

Figure 1:
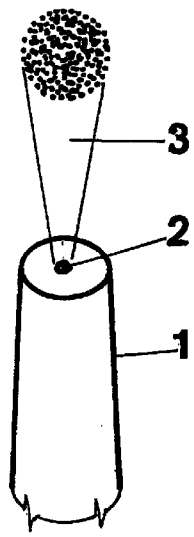
FIG. 1 schematically shows a perspective view of the end of a truncated conical distribution valve of known kind.

FIG. 1 schematically shows a perspective view of the end of a distribution valve of known kind; in FIG. 1 the body 1 (having substantially cylindrical or truncated conical shape) carrying the round distribution nozzle 2 and the substantially conical shaped jet 3, coming out from the distribution nozzle 2 in a substantially axial direction, allowing to spray a limited portion of the nasal mucosa, in particular in the zone of the nasal cavity which is immediately adjacent to the end of the body 1 where the distribution nozzle 2 is located, as clearly visible in FIG. 6, are shown.

Figure 2:
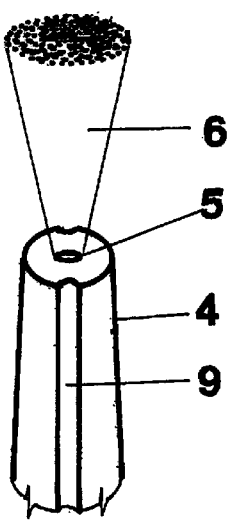
FIG. 2 schematically shows a perspective view of the end of a distribution valve having elliptical or oval section realized according to the invention.
Figure 3:
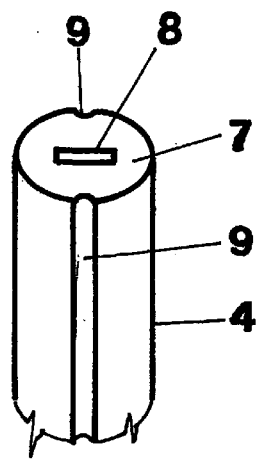
FIG. 3 schematically shows a perspective view of the end of a variation of the distribution valve of FIG. 2.
Figure 4:
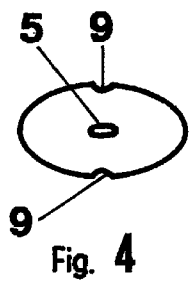
FIG. 4 schematically shows a top view of the end of the distribution valve of FIG. 2.
Figure 5:
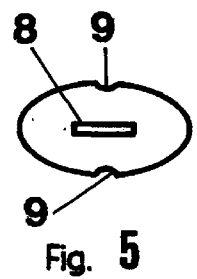
FIG. 5 schematically shows a top view of the end of the distribution valve of FIG. 3.

FIGS. 2 and 3 schematically show a perspective view of the end of a distribution valve according to the invention, including the body 4 whose section (taken along a plane orthogonal to the longitudinal symmetry axis of the body 4) has elliptical or oval shape: at the end of the body 4 there is the distribution nozzle 5 having elongated shape, which may have elliptical or oval shape (FIG. 2; better visible in the top view of FIG. 4) or slot shaped (FIG. 3; better visible in the top view of FIG. 5).

Obviously the elliptical or oval shapes forming the section of the body 4, respectively the shape of the distribution nozzle 5 (FIGS. 2 and 4), have a major symmetry axis and a minor symmetry axis, wherein the major axis has a length different from the minor axis one.

The elliptical or oval section of the body 4 and the (elliptical or slot) shape of the distribution nozzle 5 allow to overcome the above described drawbacks with reference to the distribution valves of known kind because:

the section having elliptical or oval shape of the body 4 fits the substantially elliptical or oval section of the nostril, wherein the body 4 may be inserted into only with a constant angulation: on each application the jet supplied by the nozzle 5 is therefore directed to the same portion of the nasal mucosa (repeatable application of the drug);

owing to the shape of the distribution nozzle 5 the jet 6, coming out from the nozzle 5 shows in turn a section which (as visible in FIG. 10) makes it suitable to spray in a more uniform way a wider portion of the mucosa of the nasal cavity.

Preferably but not necessarily, the size of the section having elliptical or oval shape of the body 4 is equivalent to a nostril one: the major axis of the external nostril and the vestibulum nasi vary based on the different anatomical typologies and in relation to the race and the age, so that the major axis ranges from 5 to 25 mm and the minor axis ranges from 3 to 15 mm;

the major axis of the distribution nozzle 5 having elliptical or oval shape (FIGS. 2 and 4) is about 0.92 mm (and however between about 0.77 and 1.17 mm), while the minor axis is about 0.4 mm and however ranging from about 0.3 to 0.4 mm;

the greater side of the distribution nozzle 5 having slot shape (FIGS. 3 and 5) is about 0.92 mm (and however ranging from about 0.77 to 1.17 mm), while the minor axis is about 0.4 mm and however ranging from about 0.3 to 0.4 mm.

In the here described embodiment examples, on the external surface of the body 4 having elliptical or oval section there is at least a longitudinal cavity 9 (two in the FIGS. 2–5, 7–9, 11 and 12) suitable to allow the emission of the spray (in case) supplied in excess with respect to the one absorbed (or absorbable) by the nasal mucosa and/or the fluid which vehiculated the drug itself and to let out the pressure (in case) generated inside the nostril following the spray application, thus avoiding the risk that an overpressure (at least potentially) such to damage the mucosa of the nasal septum and/or the nasal turbinates or the middle ear by the Eustachian tube may generate inside the nasal cavity.

This turns out particularly advantageous if the nasal cavity or the rhinopharyngeal one is (at least partially) obstructed by mucus (or by other organic fluid, caused for example by an inflammation of the mucosa) preventing the excess drug and/or the fluid to naturally flow down by rhinopharyngeal way.

Preferably but not necessarily the at least one longitudinal cavity 9 has semicircular section but, without leaving the field of the invention, it is possible to provide longitudinal cavities 9 having from time to time the preferred and/or the believed more functional section in consideration of a specific utilization.

Always without leaving the field of the invention it is possible not to insert the at least one longitudinal cavity 9.

FIG. 6 schematically shows an anatomical section showing the jet 3 coming out from a distribution nozzle 1 of known kind as, for example, the one illustrated in FIG. 1 and its propagation into the nasal cavity: from such a Figure one may point out that the jet 3 comes out from the nozzle 2 in a substantially axial direction spraying a limited portion of the mucosa not including (nor it may include) the zone of the nasal mucosa covering the higher part (or "roof") and the lower one (or "floor") of the nasal cavity.

FIG. 6a schematically shows a cross section of the substantially circular jet 3 coming out from a distribution nozzle 1 of known kind.

In order to spray in a uniform way the whole nasal cavity it is necessary to spray the product upwards, then to the middle part of the nasal cavity and finally downwards, varying the inclination angle of the longitudinal symmetry axis of the body 1 inside the nasal cavity.

FIG. 7 schematically shows a side view (FIG. 7a) and a top view (FIG. 7b) of an embodiment form of a distribution valve having elliptical or oval shape, differing from the FIG. 2 one essentially in that the top end of the body 4, where the distribution nozzle 5 having elliptical or oval shape is realized, is rounded (or "bell-shaped") in order to further reduce the risk to damage and/or irritate the nasal mucosa.

The rounded end of the body 4 where the distribution nozzle 5 is realized has (preferably but not necessarily) semi-elliptical or semi-oval section.

The FIGS. 7–10 moreover show the body 10, projecting with respect to the body 4 of the distribution valve, allowing the patient to more easily operate the distribution valve in order to deliver the drug in "nasal spray" form.

Figure 8:
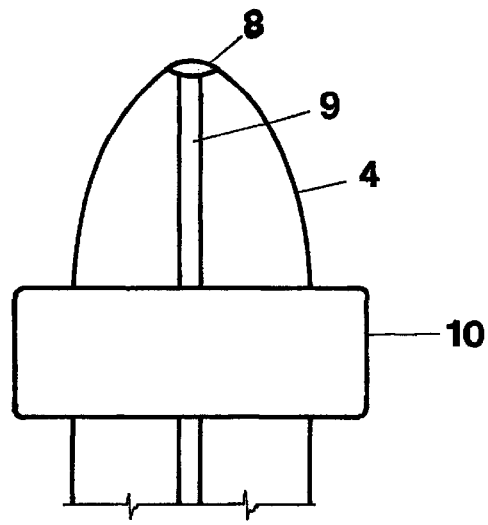
FIG. 8 schematically shows a side view of a distribution valve realized according to the invention, differing from the FIG. 3 one in that its top end is rounded.

FIG. 8 schematically shows a side view of an embodiment form of a distribution valve having elliptical or oval section, differing from the FIG. 3 one essentially in that the top end of the body 4, where the distribution nozzle 8 having slot shape is realized, is rounded (or "bell-shaped") in order to further reduce the risk to damage and/or irritate the nasal mucosa.

The top view of the distribution valve of FIG. 8 has been omitted because substantially analogous to that one illustrated in FIG. 7a.

Figure 9A:
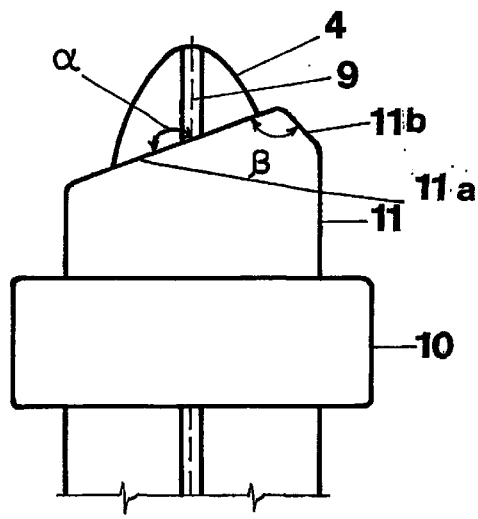
FIG. 9 schematically shows a side (FIG. 9a) view and a top (FIG. 9b) view of another distribution valve realized according to the invention.
Figure 9B:
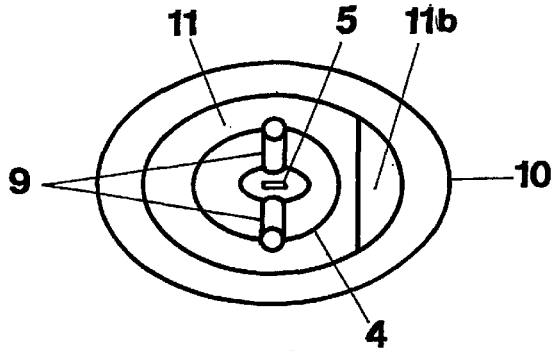

FIG. 9 schematically shows a side view (FIG. 9a) and a top view (FIG. 9b) of another form of embodiment of a distribution valve having elliptical or oval section, differing from those ones of FIGS. 7 and 8 in that it includes a further body 11 having elliptical or oval section, applied outside the body 4 of the distribution valve, whose higher surface 11a (directed towards the end of the body 4 where the distribution nozzle 5 is present) is tilted with respect to the longitudinal symmetry axis of the body 4 of a first preset angle (α) to drive and position in a more precise way the body 4 and, consequently, the jet 6.

Figure 10:
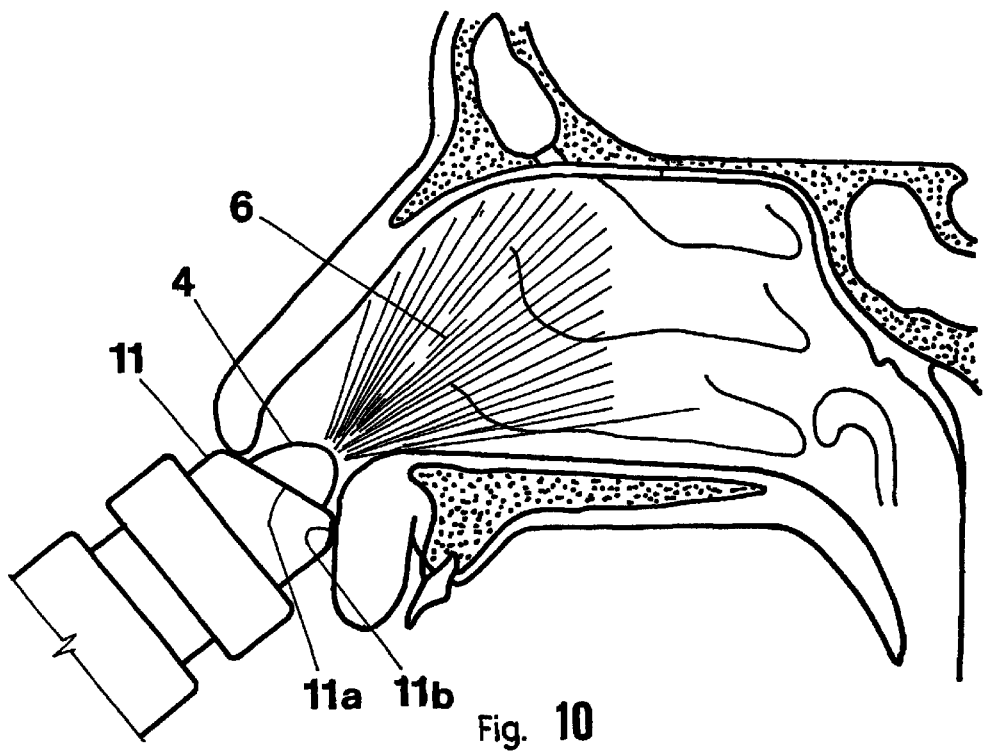
FIG. 10 schematically shows an anatomical section showing the jet coming out from the distribution nozzle of the FIG. 9.

Preferably but not necessarily the body 11 moreover shows a further tilted surface 11b, located at an end of the higher surface 11a, with respect to which it is tilted of a second preset angle (β): when the distribution valve is set to work, the tilted surface 11b of the body 11 leans on the higher lip of the patient, as better visible in FIG. 10, increasing, if necessary, the nasolabial angle which normally is about 100 degrees.

Preferably the first preset angle (α) is about 70 degrees and however ranging from about 60 to 80 degrees, while the second preset angle (β) is about 120 degrees and however ranging from about 110 to 130 degrees.

Figure 10A:
Figure 13:
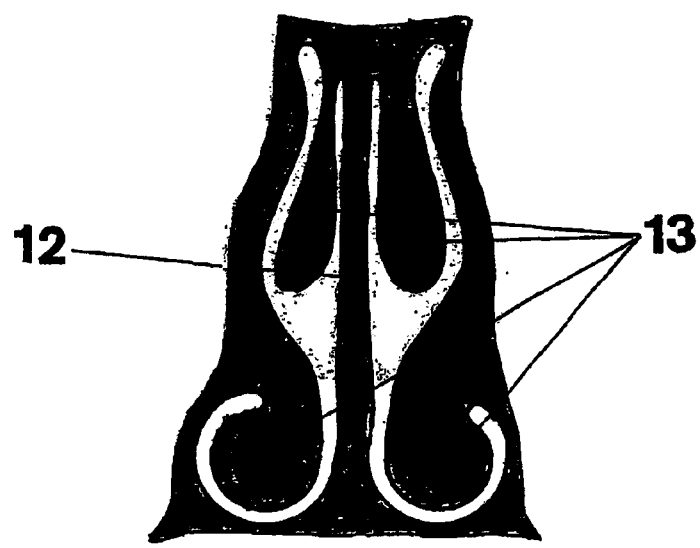
FIG. 13 shows a transverse anatomical section of the nasal cavities.

FIG. 10 schematically illustrates an anatomical section showing the jet 6 coming out from the distribution nozzle of FIG. 9; from such Figure one may point out that:

the tilted surface 11a of the body 11 leans against the edge of the external nostril, while the tilted surface 11b leans on the higher lip of the patient, driving and positioning in a precise and repeatable way the body 4;

the jet 6 coming out from the nozzle 5 has a slot shape (FIG. 10a) allowing it to deeply penetrate into the nasal cavities, which have a slot shape (FIG. 13).

Figure 11:
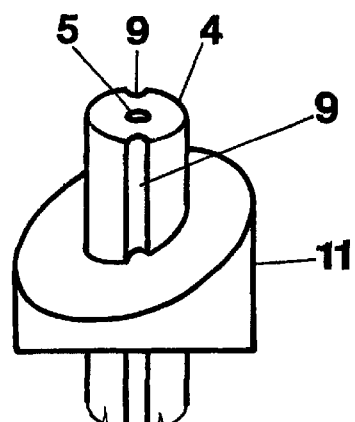
FIG. 11 schematically shows a perspective view of the end of a further distribution valve realized according to the invention, analogous to the FIG. 2 one.

FIG. 11 schematically shows a perspective view of the end of a further form of embodiment of a distribution valve having elliptical or oval section, differing from the FIG. 2 one essentially in that it also includes the body 11.

Figure 12:
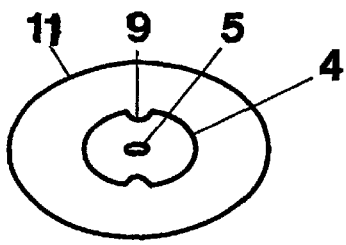
FIG. 12 schematically shows a top view of the end of the distribution valve of FIG. 11.

FIG. 12 schematically shows a top view of the end of the distribution valve of FIG. 11.

Figure 14:
FIG. 14 shows a distal section of the external nostrils and the vestibulum nasi. In the attached Figures, the corresponding elements will be identified by the same numerical references.

FIG. 13 shows an anatomical section transverse view of the nasal cavities, wherein the nasal septum 12 and the nasal turbinates 13 are pointed out; the FIG. 14 shows a distal section of the external nostrils and the vestibula nasi.

Without leaving the field of the invention it is possible for one skilled in the art to make to the distribution valve for nasal spray object of the present description all the changes and the improvements suggested by the normal experience and by the natural evolution of the art.

What is claimed:

1. Distribution valve for nasal spray including a body (4), to be inserted into a nostril, having a distribution nozzle (5, 8) for said spray, said valve having a cross section of elliptical or oval shape equivalent to a nostril's cross section and said nozzle having an elliptical or oval or slot shape, the surface of the body (4) having at least a longitudinal cavity (9) of a semicircular section, the end of the body (4) where the distribution nozzle (5, 8) is provided being optionally rounded, characterized in that the valve includes a further body (11) having elliptical or oval cross section, applied outside the body (4), the surface (11a) of the further body being nearest the nozzle is tilted in a first preset angle (α) with respect to a longitudinal symmetry axis of the body (4).

2. Distribution valve as claimed in claim 1, characterized in that the first preset angle (α) is between about 60 and 80 degrees.

3. Distribution valve as claimed in claim 1, characterized in that the first preset angle (α) is about 70 degrees.

4. Distribution valve as claimed in claim 1, characterized in that the further body (11) shows a further tilted surface (11b), tilted of a second preset angle (β) with respect to the surface (11a), suitable to lean on the higher lip of the patient when the distribution valve is set to work.

5. Distribution valve as claimed in claim 4, characterized in that the second preset angle (β) is between about 110 and 130 degrees.

6. Distribution valve as claimed in claim 4, characterized in that the second preset angle (β) is about 120 degrees.

* * * * *